United States Patent
Reisinger et al.

(10) Patent No.: US 7,091,370 B2
(45) Date of Patent: Aug. 15, 2006

(54) PROCESS FOR THE PREPARATION OF DIARYL CARBONATES

(75) Inventors: Claus-Peter Reisinger, Wixom, MI (US); Sven Michael Hansen, Leverkusen (DE); Peter Fischer, Köln (DE)

(73) Assignee: Bayer Aktiengesellschaft, Leverkusen (DE)

( * ) Notice: Subject to any disclaimer, the term of this patent is extended or adjusted under 35 U.S.C. 154(b) by 326 days.

(21) Appl. No.: 10/225,530

(22) Filed: Aug. 21, 2002

(65) Prior Publication Data

US 2003/0050496 A1    Mar. 13, 2003

(30) Foreign Application Priority Data

Aug. 24, 2001   (DE)   ............................... 101 41 622

(51) Int. Cl.
*C07C 69/96*    (2006.01)
(52) U.S. Cl. .................................................... 558/268
(58) Field of Classification Search ................. 558/268
See application file for complete search history.

(56) References Cited

U.S. PATENT DOCUMENTS

| | | | |
|---|---|---|---|
| 4,201,721 A | 5/1980 | Hallgren | 260/463 |
| 4,349,485 A | 9/1982 | Hallgren | 260/463 |
| 5,231,210 A | 7/1993 | Joyce et al. | 558/274 |
| 5,498,742 A | 3/1996 | Buysch et al. | 558/274 |
| 5,760,272 A | 6/1998 | Pressman et al. | 558/274 |
| 5,898,079 A | 4/1999 | Pressman et al. | 558/274 |
| 5,898,080 A | 4/1999 | Pressman et al. | 558/274 |
| 6,566,295 B1 * | 5/2003 | Shalyaev et al. | 502/150 |

* cited by examiner

*Primary Examiner*—Kamal A. Saeed
*Assistant Examiner*—Robert Shiao
(74) *Attorney, Agent, or Firm*—Joseph C. Gil; Aron Preis

(57) ABSTRACT

A process for the preparation of an aromatic carbonate is disclosed. The process entails reacting an aromatic hydroxy compound of the formula $R-(O-H)_k$, with carbon monoxide and oxygen, optionally in a solvent and in the presence of catalyst components, characterized in that after an initial partial charge of $R-(O-H)_k$ to the reaction mixture, the balance thereof is subsequently metered into the reaction mixture at least once in the course of the reaction.

11 Claims, No Drawings

PROCESS FOR THE PREPARATION OF DIARYL CARBONATES

FIELD OF THE INVENTION

The present application relates to a process for the preparation of diaryl carbonates (DAC).

SUMMARY OF THE INVENTION

A process for the preparation of an aromatic carbonate is disclosed. The process entails reacting an aromatic hydroxy compound of the formula $R\text{—}(O\text{—}H)_k$, with carbon monoxide and oxygen, optionally in a solvent and in the presence of catalyst components, characterized in that after an initial partial charge of $R\text{—}(O\text{—}H)_k$ to the reaction mixture, the balance thereof is subsequently metered into the reaction mixture at least once in the course of the reaction.

BACKGROUND OF THE INVENTION

The preparation of DAC by oxidative direct carbonylation of aromatic hydroxy compounds in the presence of CO, $O_2$ and a noble metal catalyst is known (see e.g. DE-OS 27 38 437, U.S. Pat. No. 4,349,485, U.S. Pat. No. 5,231,210, EP-A 667 336, EP-A 858 991, U.S. Pat. No. 5,760,272). Palladium is preferably employed as the noble metal. A cocatalyst (e.g. salts of manganese or cobalt), a base, sources of bromide, quaternary salts, various quinones or hydroquinones and drying agents can additionally be employed. The process can be carried out in a solvent.

However, the known processes do not give yields which are satisfactory for an industrial reaction and produce relatively large amounts of by-products. It is therefore desirable to provide a process which is optimized in respect of yield and product quality.

Since these are processes which are to provide a product on a large industrial scale, small optimizations already mean a great improvement.

DETAILED DESCRIPTION OF THE INVENTION

A process has now been found which allows a surprising increase in the selectivity of the reaction, i.e. the decrease in by-products with a simultaneous increase in product yield.

The invention thus provides a process for the preparation of an aromatic carbonate of the formula

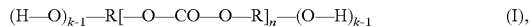

(I), wherein k represents integers of 1 to 2, preferably 1, and n represents integers from 1 to 30, preferably 1 to 10, particularly preferably 1, and R represents an aromatic radical, in which an aromatic hydroxy compound of the formula

(II), wherein R and k are as defined above,

CO and $O_2$ are reacted in a reaction mixture that optionally contains a solvent and in the presence of catalyst components, characterized in that $R\text{—}(O\text{—}H)_k$ is introduced to the reaction mixture in the course of the reaction in at least one dose subsequent to an initial amount.

The aromatic hydroxy compounds $R\text{—}(O\text{—}H)_k$ which may be reacted according to the invention are, for example, monohydroxy compounds (k=1, n=1), such as phenol, o-, m- or p-cresol, o-, m- or p-chlorophenol, o-, m- or p-ethylphenol, o-, m- or p-propylphenol, o-, m- or p-methoxyphenol, 2,6-dimethylphenol, 2,4-dimethylphenol, 3,4-dimethylphenol, 1-naphthol or 2-naphthol, or dihydroxy compounds (k=2, $1 \leq n \leq 30$, preferably $1 \leq n \leq 10$, particularly preferably $1 \leq n \leq 5$), such as resorcinol and hydroquinone, or bisphenols, such as 2,2-bis-(4-hydroxyphenyl)-propane(bisphenol A), 2,2-bis-(3,5-dimethyl-4-hydroxyphenyl)-propane, 1,1-bis-(4-hydroxyphenyl)-cyclohexane, 1,1-bis-(4-hydroxyphenyl)-3,3,5-trimethylcyclohexane or 6,6'-dihydroxy-3,3,3',3'-tetramethyl-1,1'-spiro(bis)-indane, 2,4'-hydroxybiphenyl or 4,4'-hydroxybiphenyl. $R\text{—}(O\text{—}H)_k$ may have various substituents on the aromatic nucleus R. In the case of substitution of the aromatic hydroxy compound, this is generally by 1 to 3 substituents with the definition of $C_1\text{-}C_{18}$-alkyl, $C_6\text{-}C_{18}$-aryl, $C_7\text{-}C_{18}$-acralkyl, $C_1\text{-}C_{18}$-alkoxy, fluorine, chlorine or bromine, wherein the substituents, in the case of the hydrocarbons, may in their turn be mono- or polysubstituted by the groups mentioned.

Mixtures of various $R\text{—}(O\text{—}H)_k$ may be used, but the use of a single compound $R\text{—}(O\text{—}H)_k$ is preferred. Bisphenol A is preferably employed. The above mentioned monohydroxy compounds are furthermore preferably employed, particularly preferably phenol or o-, m- and p-cresol, very particularly preferably phenol.

The reaction system of the oxidative direct carbonylation typically comprises several of the following catalyst components:

a) a metal salt of group VIIIB,
b) at least one second metal salt,
c) a source of bromide,
d) a base and
e) organic cocatalysts.

The platinum metal catalysts a) which are suitable for the process according to the invention comprise at least one noble metal of group VIII, preferably palladium. It may be added in various forms in the process according to the invention. Palladium may be employed in metallic form, e.g. as palladium black or on a support, such as Pd/C, Pd/$Al_2O_3$ or Pd/$SiO_2$, or preferably in the form of palladium compounds of oxidation levels 0 and +2, such as, for example, palladium(II) acetylacetonate, halides, carboxylates of $C_2\text{-}C_{18}$-carboxylic acids, dicarboxylates, such as oxalate, nitrate, sulfate or oxides, or palladium complexes which may comprise, for example, carbon monoxide, olefins, amines, nitriles, phosphorus compounds and halides. Palladium bromide and palladium acetylacetonate are particularly preferred.

The amount of platinum metal catalyst is not limited in the process according to the invention. Preferably, catalyst is added in an amount such that the concentration of the metal in the reaction mixture is 1 to 3,000 ppm, and concentrations of 5 to 500 ppm are particularly preferred.

A metal of groups III A, III B, IV A, IV B, V B, I B, II B, VI B or VII B, of the rare earth metals (atomic numbers 58–71) and of the iron group of the periodic table of the elements (Mendeleev), optionally also mixtures thereof, is used as the second metal salt b) it being possible for the metal to be employed in various oxidation levels. (See e.g. U.S. Pat. No. 5,142,086, U.S. Pat. No. 5,231,210, U.S. Pat. No. 5,284,964, EP-A 350 697, EP-A 350 700, U.S. Pat. No. 5,336,803) Pb, Ti, Mn, Cu, Co, V, Zn, Ce and Mo are preferably employed. Without limiting the process according to the invention, lead(II), manganese(II), manganese(III), copper(I), copper(II), cobalt(II), cobalt(III), vanadium(III) and vanadium(IV) may be used. The metals may be employed, for example, as halides, oxides, carboxylates of $C_2$-$C_{18}$-carboxylic acids, diketonates or nitrates and as complex compounds which may comprise, for example, carbon monoxide, olefins, aromatic and aliphatic mono- or polyamines, phosphorus compounds, pyridines, bipyridines, terpyridines, quinolines, isoquinolines, cryptands, Schiff's bases and halides. Mn, Cu, Mo, Pb and Ce are particularly preferably employed. Manganese compounds are very particularly preferably used in the process according to the invention, particularly preferably complexes of manganese (II) and manganese(III), very particularly preferably maganese(II) acetylacetonate or manganese(III) acetylacetonate, and manganese(II) bromide.

The metal salt (b) which may also be formed in situ, is added in an amount such that its concentration is in the range from 0.0001 to 20 wt. % of the reaction mixture, and the concentration range of 0.001 to 5 wt. % is preferred, particularly preferably 0.005 to 2 wt. %.

The bromide compounds c) employed in the context of the present invention are, for example, the alkali metal bromides or alkaline earth metal bromides, but preferably the bromide salts of organic cations. The organic cations may be, for example, ammonium, guanidinium, phosphonium or sulfonium salts substituted by organic radicals, and optionally also mixtures thereof. Ammonium, guanidinium, phosphonium and sulfonium salts which contain $C_6$- to $C_{18}$-aryl, $C_7$- to $C_{18}$-aralkyl and/or $C_1$- to $C_{20}$-alkyl radicals as organic radicals are suitable for use in the process according to the invention. Ammonium salts which carry $C_6$- to $C_{18}$-aryl, $C_7$- to $C_{18}$-aralkyl and/or $C_1$- to $C_{20}$-alkyl radicals as organic radicals are preferably employed in the process according to the invention, and tetrabutylammonium bromide, tetraphenylphosphonium bromide and tetrabutylphosphonium bromide are particularly preferred. The amount of such a quaternary salt may be, for example, 0.1–20 wt. %, based on the weight of the reaction mixture. This amount is preferably 0.5–15 wt. %, particularly preferably 1–5 wt. %.

Bases, component d) which may be employed for the process according to the invention are alkali metal hydroxides, alkali metal salts or quaternary salts of weak acids, such as alkali metal tert-butylates, or alkali metal salts or quaternary salts of aromatic hydroxy compounds of the formula (II), in which R has the abovementioned meaning. An alkali metal salt or quaternary salt of the aromatic hydroxy compound of the formula (II) which is also to be reached to give the organic carbonate, for example tetrabutylammonium or potassium phenolate, is very particularly preferably used.

The alkali metal salts may be salts of lithium, sodium, potassium, rubidium or caesium. Lithium, sodium and potassium salts are preferably employed, particularly preferably potassium salts, and very particularly preferably potassium phenolate.

The quaternary salts may be ammonium, phosphonium, pyridinium, sulfonium or guanidinium salts which have $C_6$- to $C_{18}$-aryl, $C_7$- to $C_{18}$-aralkyl and/or $C_1$- to $C_{20}$-alkyl radicals as organic radicals. The radicals may all be identical or different, and mixtures of several quaternary salts may optionally also be employed. The same cation which is suitable for the bromide for component c) may optionally be employed here. Tetraphenylphosphonium, tetrabutylammonium and tetrabutylphosphonium are furthermore preferred, and tetrabutylammonium is particularly preferred.

Alternatively, trialkylamine bases, such as tributylamine, diisopropylethylamine, DBU or DBN, may also be used.

The base d) is added in an amount independent of the stoichiometry. The ratio of platinum metal, e.g. palladium, to base is preferably chosen such that 0.1 to 5,000, preferably 1 to 1,000, particularly preferably 10 to 300 equivalents of base are employed per mol of platinum metal, e.g. palladium.

Organic cocatalysts e) which may be employed include various terpyridines, phenanthrolines, quinolines and isoquinolines, semiquinones, hydroquinones and quinones, or the organic cocatalysts mentioned in EP1024132-A1 are employed.

Examples are 2,2':6',2''-terpyridine, 4'-methylthio-2,2': 6'2'-terpyridine, 2,2':6',2''-terpyridine N-oxide, 1,10-phenanthroline, 2,4,7,8-tetramethyl-1,10-phenanthroline, 4,7-diphenyl-1,10-phenanthroline, catechol, 1,2-quinone, hydroquinone, p-benzoquinone, anthraquinone, 9,10-dihydroxyanthracene and phenanthrenequinone.

According to the invention, the hydroxyaromatic R—(O—H)$_k$ is metered in one or more increments after an initial amount is introduced to the reaction mixture. An initial, or start concentration, established within the first hour of reaction time, of about 10 to 80 wt. % of the total amount is preferably started with, and the remaining amount is added in one or more increments. The start concentration is particularly preferably about 30 to 70 wt. %. The subsequent addition is preferably in one to about ten increments. Preferably these subsequent additions are made in approximately equidistant time intervals. An addition of the last portion at a point in time which is before about 90% of the total reaction time or average residence time is preferred, particularly preferably before about 80%.

The amount of R—(O—H)$_k$ subsequently metered in may also be passed in continuously, for example by slowly pumping in a solution. A start concentration, established within the first hour of reaction time, of about 10 to 80 wt. % of the total amount is preferably started with, particularly preferably 30 to 70 wt. %, and the remaining amount is then metered in continuously. Various times/concentration metering profiles may be established, e.g. a larger amount per unit time may be metered in at the start than towards the end of the reaction time or vice versa. An addition of the amount of R—(O—H)$_k$ which is linear with respect to time, in which the amount added per time interval remains approximately constant, is preferred. The addition may be started and interrupted at any desired points in time in the course of the reaction or the average residence time.

An ending of the metering at a point in time which is before about 90% of the total reaction time or average residence time is preferred, particularly preferably before about 80%.

The R—(O—H)$_k$ may be metered in as a solid or as a liquid or solution. R—(O—H)$_k$ may optionally be metered in over heated feed lines. However, the addition as a solution in an inert solvent is preferred.

The process according to the invention may be carried out both in a continuous and in a discontinuous manner.

In a discontinuous procedure, R—(O—H)$_k$ is metered in at a point in time after the start of the reaction in the reactor.

In the case of a continuous procedure, R—(O—H)$_k$ may be metered in, for example, in a cascade of a plurality of reaction vessels, into at least one of the 2nd or any subsequent reactors in the course of reaction.

The process according to the invention for carbonate formation is carried out at a reaction temperature of 30 to 200° C., preferably 50 to 150° C., particularly preferably 60 to 130° C., under a reaction pressure of 1 to 200 bar, preferably 1 to 50 bar, particularly preferably 1 to 10 bar.

Hydrocarbons, halogenated hydrocarbons and aromatic solvents, such as chlorobenzene, dichlorobenzene, fluorobenzene, benzene, toluene, anisole, cyclohexane, petroleum ether, methylene chloride or 1,2-dichloroethane, dipolar aprotic solvents, such as dimethylacetamide, acetonitrile or N-methylpyrrolidone, ethers, such as dioxane, tetrahydrofuran, t-butyl methyl ether and etherified glycols, and optionally also mixtures of various solvents may be used as the inert organic solvent. Chlorobenzene is particularly preferably employed. The reaction mixture may comprise the inert solvent in an amount of 1 to 99%, preferably 20 to 98%, particularly preferably 40 to 98% relative to the weight of the mixture.

The composition of the reaction gases carbon monoxide and oxygen may be varied within wide limits, but a $CO:O_2$ molar ratio (standardized to CO) of 1:0.001 to 1:1, preferably 1:0.01 to 1:0.5, and particularly preferably 1:0.02 to 1:0.3, is expediently established. The oxygen partial pressure at these molar ratios is high enough to enable achieving high space/time yields.

All the starting reactants and components of the reaction mixture may be contaminated with impurities from their preparation and storage, but in the context of the purity of the end product it is desirable to use chemicals which are as clean as possible. The reaction gases also are not subject to particular purity requirements. Thus, synthesis gas may be used as the source of CO and air as the $O_2$ carrier, but it is to be ensured that no catalyst poisons, such as e.g. sulfur or compounds thereof, are introduced. The gases may be diluted with one or more other gases, such as nitrogen, argon, carbon dioxide or hydrogen. In a preferred embodiment of the process according to the invention, pure CO and pure oxygen are used.

In another embodiment, instead of the homogeneous catalyst system heterogeneous catalysts in which the platinum metal or the platinum metal and/or the cocatalyst are applied to a heterogeneous support are employed as powders or shaped articles. The other components of the catalysts system, such as the base, the quaternary compound and optionally the cocatalyst, are furthermore dissolved homogeneously in the reaction solution. The proportion of the platinum metal in the total weight of the heterogeneous catalyst is 0.01 to 15 wt. %, preferably 0.05 to 10 wt. %, calculated as platinum metal.

At least one metal compound of the abovementioned type is employed as cocatalysts on the catalyst support.

The proportion of the amount of cocatalyst in the total weight of the heterogeneous catalyst is 0.01 to 15 wt. %, preferably 0.05 to 10 wt. %, calculated as the metal.

Suitable catalyst supports are one or more metal oxides from the group consisting of V, Mn, Ti, Cu, Zr, La and the rare earth metals (atomic numbers 58–71), both in the sense of chemically uniform pure substances and as a mixture, as well as iron and cobalt oxides, nickel, aluminium, silicon and magnesium oxide, zeolites and active charcoals. If the supported catalyst is employed as a powder, for mixing the reaction compounds the stirred containers to be used are equipped with stirrers which may be used for this, or are designed as a bubble column reactor.

If supported catalyst powders are used as a suspension in stirred vessels or bubble columns, amounts of 0.001 to 50 wt. %, preferably 0.01 to 20 wt. %, particularly preferably 0.1 to 10 wt. % of supported catalyst powder, based on the amount of aromatic hydroxy compound employed, are used.

In preferred embodiments, the heterogeneous supported catalyst is employed in a fixed location in stirred containers, a bubble column, a trickle phase reactor or cascades of these reactors. It is then completely unnecessary to separate off the supported catalyst.

Suitable reactors for the process according to the invention with a homogeneous or heterogeneous catalyst are stirred tanks, autoclaves and bubble columns, it being possible for these to be employed as individual reactors or as a cascade. In a cascade, 2 to 15, preferably 2 to 10, particularly preferably 2 to 5 reactors may be connected in series.

For mixing the reaction components, the stirred containers to be used according to the invention are equipped with stirrers suitable for this. Such stirrers are known to the expert. Examples which may be mentioned are: disc, impeller, propeller, paddle, MIG and intermig stirrers, tubular stirrers and various types of hollow stirrers. Preferred stirrers are those which allow effective mixing of gases and liquids, for example hollow tube gassing stirrers, propeller stirrers etc.

The following types of bubble columns may be employed in the process according to the invention: simple bubble columns, bubble columns with inserts, such as e.g.: bubble columns with parallel chambers, cascade bubble columns with sieve trays or single-hole trays, bubble columns with packing, with static mixers, pulsating sieve tray bubble columns, loop reactors, such as e.g.: mammoth loop reactors, outflow loop reactors, jet loop reactors, free jet reactors, nozzle reactors, bubble columns with liquid immersion jets, outflow-inflow bubble columns and further bubble column reactors known to the expert (Chem. Ing. Tech. 51 (1979) no. 3, p. 208–216; W.-D. Deckwer, Reaktionstechnik in Blasensäulen [Reaction Techniques in Bubble Columns], Otto Salle Verlag 1985).

In a preferred embodiment, bubble column reactors and bubble column cascades which allow effective mixing of gas and liquids, such as, for example, cascade bubble columns and loop reactors, are employed. Distributing and redispersing organs may be attached along the longitudinal axis of the bubble column reactors to maintain good thorough mixing of liquid and reaction gas. Single hole trays, perforated trays, sieve trays and further inserts known to the expert are employed as fixed redispersing means. Conventional devices, such as porous sintered plates, perforated plates, sieve trays, inserted tubes, nozzles, gassing rings and further dispersing devices known to the expert may be employed for the initial dispersing of the reaction gas in the liquid phase during metering in.

The process according to the invention may be carried out in various variants. One possibility includes the discontinuous procedure. In this, CO and oxygen are passed into the reaction mixture either through a gassing stirrer, as in the case of a stirred tank, or through other known gas distribution means. When the optimum conversion is reached, the reaction mixture is removed from the reactor or optionally worked up in the reactor. If pulverulent supported catalysts are used, these may be separated off from the reaction mixture, e.g. by filtration, sedimentation or centrifugation.

Embodiments which utilize the parameters, compounds, definitions and explanations mentioned as preferred, particularly preferred or very particularly preferred are preferred, particularly preferred or very particularly preferred.

However, the definitions, parameters, compounds and explanations mentioned above generally or mentioned in preferred ranges may also be combined as desired with one another, that is to say between the particular ranges and preferred ranges.

Supported catalysts used in discontinuous experiments may be employed repeatedly, optionally without purification, with the same starting substances. In the case of a continuous procedure, the supported catalysts employed may remain in the reactor over a long period of time and may optionally be regenerated.

A continuous procedure in a single reactor or in a cascade of several reactors is preferably employed. If heterogeneous catalysts of fixed location are used, these may remain in the reactor over a long period of time and may optionally also be regenerated there.

EXAMPLES

The reaction components are analysed by gas chromatography, the weights of the components are determined by means of an internal standard. The selectivity is calculated by adding the amount of residual phenol contained in the reaction mixture and phenol converted into DPC and dividing the sum by the total amount of phenol employed. The phenol not included in this has been converted into by-products.

Example 1

0.03 mmol palladium(II) bromide, 7.5 mmol tetrabutylammonium bromide, 0.7 mmol manganese trisacetylacetonate and 16 g phenol are initially introduced into 50 ml chlorobenzene in an autoclave and the mixture is heated to 80° C. while passing through carbon monoxide. 7.5 mmol tetrabutylammonium phenolate in 30 ml chlorobenzene are then added. A gas mixture of carbon monoxide and oxygen (97:3 vol. %) is passed through at 90° C./3 bar. After 15 min an additional 8.2 g phenol in 12.3 g chlorobenzene are pumped in continuously and uniformly in the course of 90 min. After 2 h the reaction is interrupted and the reaction mixture is analysed by means of GC. The results are summarized in Table. 1.

Comparison Example 1

0.03 mmol palladium(II) bromide, 7.5 mmol tetrabutylammonium bromide, 0.7 mmol manganese trisacetylacetonate and 24.2 g phenol are initially introduced into 50 ml chlorobenzene in an autoclave and the mixture is heated to 80° C. while passing through carbon monoxide. 7.5 mmol tetrabutylammonium phenolate in 30 ml chlorobenzene are then added. A gas mixture of carbon monoxide and oxygen (97:3 vol. %) is passed through at 90° C./3 bar. After 2 h the reaction is interrupted and the reaction mixture is analysed by means of GC. The results are summarized in Table 1.

TABLE 1

|  | Ex. 1 | Comp. 1 |
| --- | --- | --- |
| Conversion of phenol [%] | 36.9 | 35.9 |
| Selectivity [%] | 87.1% | 83.8% |
| Space/time yield [g/l/h] | 35.1 | 33.5 |
| Turn-over number Pd | 1,216 | 1,022 |

Although the invention has been described in detail in the foregoing for the purpose of illustration, it is to be understood that such detail is solely for that purpose and that variations may be made therein by those skilled in the art without departing from the spirit and scope of the invention except as it may be limited by the claims.

What is claimed is:

1. A process for the preparation of an aromatic carbonate of the formula

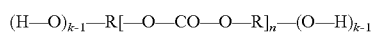

wherein k represents integers of 1 to 2 and n represents integers from 1 to 30 and R represents an aromatic radical, comprising reacting an aromatic hydroxy compound of the formula R—(O—H)$_k$, with carbon monoxide and oxygen, optionally in a solvent and in the presence of catalyst components, characterized in that after an initial partial charge of R—(O—H)$_k$ to the reaction mixture, the balance thereof is subsequently metered into the reaction mixture at least once in the course of the reaction, wherein the amount of R—(O—H)$_k$ introduced as an initial partial charge is about 10 to 80% of the total amount metered in.

2. The process according to claim 1, in which

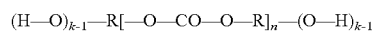

is diphenyl carbonate and R—(O—H)$_k$ is phenol.

3. The process according to claim 1, in which the metering of R—(O—H)$_k$ is ended at a point in time which is before about 90% of the total reaction time or average residence time.

4. The process according to claim 1 where R—(O—H)$_k$, is bisphenol A.

5. The process according to claim 1 in which the balance is subsequently metered into the reaction mixture in one to ten increments.

6. The process according to claim 1, in which the subsequent metering takes place continuously.

7. A process for the continuous preparation of diaryl carbonates conforming to

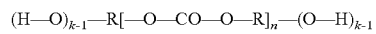

wherein k represents integers of 1 to 2 and n is 1 to 30 and R represents an aromatic radical, comprising reacting in a cascade containing a plurality of reaction vessels a hydroxyaryl, carbon monoxide and oxygen, in optional solvent and in the presence of catalyst components, characterized in that the hydroxyaryl that conforms to

is metered into at least two of said plurality of vessels including the first.

8. The process of claim 7 wherein the hydroxyaryl is at least one member selected from the group consisting of phenol, cresol, chlorophenol, ethylphenol, propylphenol, methoxyphenol, 2,6-dimethylphenol, 2,4-dimethylphenol, 3,4-dimethylphenol, 1-naphthol, 2-naphthol, resorcinol hydroquinone, and bisphenol.

9. The process of claim 8 wherein the bisphenol is a member selected from the group consisting of 2,2-bis-(4-hydroxyphenyl)-propane, 2,2-bis-(3,5-dimethyl-4-hydroxyphenyl)-propane, 1,1-bis-(4-hydroxy-phenyl)-cyclohexane, 1,1-bis-(4-hydroxyphenyl)-3,3,5-trimethyl-cyclohexane, 6,6'-dihydroxy-3,3,3',3'-tetramethyl-1,1'-spiro(bis)-indane, 2,4'-hydroxybiphenyl and 4,4'-hydroxybiphenyl.

10. The process according to claim 7 in which

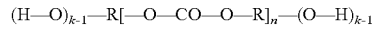

is diphenyl carbonate and the hydroxyarly is phenol.

11. A high selectivity process for the preparation of an aromatic carbonate of the formula

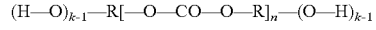

wherein k represents integers of 1 to 2 and n represents integers from 1 to 30 and R represents an aromatic radical, comprising reacting an aromatic hydroxy compound of the formula R—(O—H)$_k$, with carbon monoxide and oxygen, optionally in a solvent and in the presence of catalyst components, characterized in that after an initial partial charge of R—(O—H)$_k$ to the reaction mixture, the balance thereof is subsequently metered into the reaction mixture at least once in the course of the reaction, said selectivity higher than 83.8%.

* * * * *